US006182666B1

(12) United States Patent
Dobak, III (10) Patent No.: US 6,182,666 B1
(45) Date of Patent: Feb. 6, 2001

(54) CRYOSURGICAL PROBE AND METHOD FOR UTERINE ABLATION

(75) Inventor: John D. Dobak, III, Del Mar, CA (US)

(73) Assignee: CryoGen, Inc., San Diego, CA (US)

( * ) Notice: Under 35 U.S.C. 154(b), the term of this patent shall be extended for 0 days.

(21) Appl. No.: 09/181,114

(22) Filed: Oct. 28, 1998

Related U.S. Application Data (63) Continuation-in-part of application No. 08/774,148, filed on Dec. 26, 1996, now Pat. No. 5,910,104.

(51) Int. Cl.$^7$ .................................................. A61B 19/00

(52) U.S. Cl. ............................. 128/898; 606/24; 606/23

(58) Field of Search .................. 606/20, 26; 128/898

(56) References Cited

U.S. PATENT DOCUMENTS

| | | |
|---|---|---|
| 2,319,542 | 5/1943 | Hall . |
| 2,672,032 | 3/1954 | Towse . |
| 3,270,744 | * 9/1966 | katz et al. ............................. 606/24 |
| 3,272,203 | 9/1966 | Chato . |
| 3,273,356 | 9/1966 | Hoffman . |
| 3,298,371 | 1/1967 | Lee . |
| 3,368,549 | 2/1968 | Armao . |
| 3,398,738 | 8/1968 | Lamb et al. . |
| 3,401,533 | 9/1968 | Maybury . |
| 3,431,750 | 3/1969 | LeFranc . |
| 3,439,680 | 4/1969 | Thomas . |
| 3,477,434 | 11/1969 | Hood, Jr. et al. . |
| 3,536,075 | 10/1970 | Thomas, Jr. . |
| 3,613,689 | 10/1971 | Crump et al. . |
| 3,630,203 | 12/1971 | Sellinger et al. . |
| 3,662,755 | 5/1972 | Rautenbauch et al. . |
| 3,696,813 | 10/1972 | Wallach . |
| 3,729,945 | 5/1973 | Linnett . |
| 3,736,937 | 6/1973 | Basiulis . |

(List continued on next page.)

FOREIGN PATENT DOCUMENTS

| | | |
|---|---|---|
| 0 271 989 | 11/1990 | (EP) . |
| 0624347 | * 11/1994 | (EP) . |
| 1465540 | 1/1967 | (FR) . |
| 1468862 | 1/1967 | (FR) . |
| 2 482 445 | 3/1980 | (FR) . |
| 2477406 | 9/1981 | (FR) . |
| 1 336 892 | 11/1973 | (GB) . |
| 2 026 324 | 2/1980 | (GB) . |
| 2 080 117 | 2/1982 | (GB) . |
| 2 093 964 | 9/1982 | (GB) . |
| 2 283 678 | 5/1995 | (GB) . |
| 2 289 412 | 11/1995 | (GB) . |
| 2 289 413 | 11/1995 | (GB) . |
| 2 289 414 | 11/1995 | (GB) . |

(List continued on next page.)

OTHER PUBLICATIONS

Answer, Affirmative Defenses, and Counterclaims of Defendant Johnson & Johnson to CryoGen's First Amended Complaint for Infringement of U.S. Patent Nos. 5,758,505 & 5,910,104, *CryoGen, Inc. v. Johnson & Johnson, Inc.*, Case No. C–99–02471 VRW (N.D. Cal. Aug. 31, 1999).

Answer, Affirmative Defenses, and Counterclaims of Defendants FemRx and Ethicon to CryoGen's First Amended Complaint for Infringement of U.S. Patent Nos. 5,758,505 & 5,910,104, *CryoGen, Inc. v. Johnson & Johnson, Inc.*, Case No. C–99–02471 VRW (N.D. Cal. Jul. 1, 1999).

(List continued on next page.)

*Primary Examiner*—Michael Peffley
(74) *Attorney, Agent, or Firm*—Gerald W. Spinks (57) ABSTRACT

A cryosurgical probe incorporating various forms of auxiliary instrumentation mounted on the catheter or conductive tip, such as a temperature sensor, a heater, an ultrasonic transducer, or an optical element of a viewing, illumination, or laser system, and a method for employing such a probe for ablation of uterine tissue.

4 Claims, 9 Drawing Sheets

U.S. PATENT DOCUMENTS

| | | |
|---|---|---|
| 3,750,417 | 8/1973 | Johannes et al. . |
| 3,768,273 | 10/1973 | Missimer . |
| 3,786,814 | 1/1974 | Armao . |
| 3,827,436 | 8/1974 | Stumpf et al. . |
| 3,889,680 | 6/1975 | Armao . |
| 3,913,581 | 10/1975 | Ritson et al. . |
| 3,924,628 | 12/1975 | Droegemueller et al. . |
| 3,932,154 | 1/1976 | Coers et al. . |
| 3,971,383 | 7/1976 | van Gerven . |
| 4,015,606 | 4/1977 | Mitchiner et al. . |
| 4,206,609 | 6/1980 | Durenec . |
| 4,207,897 | 6/1980 | Lloyd et al. . |
| 4,211,231 | 7/1980 | Rzasa . |
| 4,275,734 | 6/1981 | Mitchiner . |
| 4,377,168 | 3/1983 | Rzasa et al. . |
| 4,601,296 | 7/1986 | Yerushalmi . |
| 4,646,722 | 3/1987 | Silverstein et al. . |
| 4,781,033 | 11/1988 | Steyert et al. . |
| 4,809,678 | 3/1989 | Klein . |
| 4,829,785 | 5/1989 | Hersey . |
| 4,840,043 | 6/1989 | Sakitani et al. . |
| 4,875,346 | 10/1989 | Jones et al. . |
| 4,878,485 | 11/1989 | Adair . |
| 4,990,412 | 2/1991 | Hersey . |
| 5,061,246 | 10/1991 | Anapliotis . |
| 5,063,747 | 11/1991 | Jones et al. . |
| 5,077,979 | 1/1992 | Skertic et al. . |
| 5,078,713 | 1/1992 | Varney . |
| 5,101,894 | 4/1992 | Hendricks . |
| 5,139,496 | 8/1992 | Hed . |
| 5,147,355 | 9/1992 | Friedman et al. . |
| 5,150,579 | 9/1992 | Hingst . |
| 5,157,938 | 10/1992 | Bard et al. . |
| 5,159,925 * | 11/1992 | Neuwirth et al. ................... 606/28 |
| 5,193,349 | 3/1993 | Laverman et al. . |
| 5,207,674 | 5/1993 | Hamilton . |
| 5,237,984 | 8/1993 | Williams, III et al. . |
| 5,275,595 | 1/1994 | Dobak, III . |
| 5,281,212 | 1/1994 | Savage et al. . |
| 5,281,213 | 1/1994 | Milder et al. . |
| 5,281,215 | 1/1994 | Milder . |
| 5,281,217 | 1/1994 | Edwards et al. . |
| 5,301,657 | 4/1994 | Lafferty et al. . |
| 5,324,286 | 6/1994 | Fowle . |
| 5,334,181 | 8/1994 | Rubinsky et al. . |
| 5,337,572 | 8/1994 | Longsworth . |
| 5,365,750 | 11/1994 | Greenthal . |
| 5,402,768 | 4/1995 | Adair . |
| 5,403,309 * | 4/1995 | Coleman et al. ................... 606/20 |
| 5,408,992 | 4/1995 | Hamlin et al. . |
| 5,423,807 | 6/1995 | Milder . |
| 5,476,090 | 12/1995 | Kishi . |
| 5,522,870 | 6/1996 | Ben-Zion . |
| 5,573,532 | 11/1996 | Chang et al. . |
| 5,595,065 | 1/1997 | Boiarski et al. . |
| 5,617,739 | 4/1997 | Little . |
| 5,624,392 | 4/1997 | Saab . |
| 5,644,502 | 7/1997 | Little . |
| 5,658,276 * | 8/1997 | Griswold ................... 606/24 |
| 5,667,505 * | 9/1997 | Straus ................... 606/24 |
| 5,674,218 | 10/1997 | Rubinsky et al. . |
| 5,690,605 | 11/1997 | Hamlin et al. . |
| 5,724,832 | 3/1998 | Little et al. . |
| 5,741,248 * | 4/1998 | Stern et al. ................... 606/21 |

FOREIGN PATENT DOCUMENTS

| | | |
|---|---|---|
| 2 289 510 | 11/1995 | (GB) . |
| 57-126430 | 8/1982 | (JP) . |
| 333857 | 4/1974 | (SU) . |
| 333858 | 4/1974 | (SU) . |
| 527467 | 9/1976 | (SU) . |
| 534484 | 11/1976 | (SU) . |
| 565052 | 7/1977 | (SU) . |
| 573496 | 9/1977 | (SU) . |
| 627154 | 8/1978 | (SU) . |
| 637417 | 12/1978 | (SU) . |
| 676604 | 7/1979 | (SU) . |
| 768795 | 10/1980 | (SU) . |
| 802348 | 2/1981 | (SU) . |
| 802349 | 2/1981 | (SU) . |
| 802350 | 2/1981 | (SU) . |
| 802351 | 2/1981 | (SU) . |
| 832268 | 5/1981 | (SU) . |
| 839516 | 6/1981 | (SU) . |
| 918298 | 4/1982 | (SU) . |
| 966107 | 10/1982 | (SU) . |
| 1054400 | 1/1983 | (SU) . |
| 1026795 | 7/1983 | (SU) . |
| 1026796 | 7/1983 | (SU) . |
| 1089099 | 4/1984 | (SU) . |
| 1090699 | 5/1984 | (SU) . |
| 1134856 | 1/1985 | (SU) . |
| 1158567 | 5/1985 | (SU) . |
| 1189434 | 11/1985 | (SU) . |
| 1437012 | 11/1988 | (SU) . |
| 1774140 | 11/1992 | (SU) . |
| WO 93/04647 | 3/1993 | (WO) . |
| WO 93/08753 | 5/1993 | (WO) . |
| WO 95/13025 | 5/1995 | (WO) . |
| WO 95/30379 | 11/1995 | (WO) . |
| WO 95/30380 | 11/1995 | (WO) . |
| WO 99/65410 * | 12/1999 | (WO) . |

OTHER PUBLICATIONS

Answer and Counterclaims of Defendant and Counterclaimant MMR Technologies, Inc. to First Amended Complaint for Infringement of U.S. Patent Nos. 5,758,505 & 5,910,104, *CryoGen, Inc. v. Johnson & Johnson, Inc.*, Case No. C–99–02471 VRW (N.D. Cal. Jul. 1, 1999).

Supplemental Responses and Objections of FemRx, Inc., Ethicon, Inc., and Johnson & Johnson to CryoGen, Inc.'s Second Set of Interrogatories, *CryoGen, Inc. v. Johnson & Johnson, Inc.*, Case No. C–99–02471 VRW (N.D. Cal. Jul. 1, 1999), Case No. C–99–02471 VRW (N.D. Cal.) at 4–7.

*Military & Commercial Applications for Low Cost Cryocoolers*, Electronic Industries Association Cryelectronics Division (Jan. 31 and Feb. 1, 1996), CRY005604–006036.

Docket Sheet (updated Mar. 30, 2000), *CryoGen, Inc. v. Johnson & Johnson, Inc.*, Case No. C99–02471 VRW (N.D. Cal. filed May 25, 1999).

Docket Sheet (updated Mar. 30, 2000), *FemRx, Inc. v. CryoGen, Inc.*, Case No. C98–02330 VRW (N.D. Cal. filed Jun. 8, 1998).

Cahan, William G. et al., *Cryosurgery of the Unterine Cavity*, Am.J. Obst. & Gynec. 138–153 (Sep. 1, 1967).

Abstract 907,054; A.V. Mostitskiy.

S. Bard, *A Two–Stage 80 K/140 K Sprption Cryocooler*, Proceedinngs of the 12th International Cryogenic Engineering Conference, p. 626–630. (R.G. Scurlock and C.A. Bailey, eds.) Butterworth, Guilford, UK 1988);.

J. Baust; *Underlying Mechanism of Damage and New Concepts in Bryosurgery*, Cryosurgery: Mechanisms and Applications, p. 21–36 (International Institute of Refrigeration, Paris 1995).

E. Bodio, *The application of Multicomponent Gaseous Mixtures in Linde–Hampson Coolers*, Wroclaw Institute of Tech. (1985); Partial translation to English.

V. M. Brojanski; *Developments in Cryotechnology to 2000*; May 1989; pp. 193–195; 16th Cryotechnology Congress; Translated to English.

Z. Chang; *Optimization of Cryosurgical Instrumentation for Use in Minimally Invasive Prostate Surgery*, 1993; pp. 45–55; Recent Advances in Cryogenic Engineering.

W. Bald; *Cryogenic Surgery*; pp. 1383–1434, Reports on Progress in Physics; date unknown.

W. Droegemueller; *Cryocoagulation of the Endometrium at the Uterine Cornua*; May 1978; pp. A58–A66; American Journal of Obstetrics and Gynecology.

A. Gage; *Cryosurgery*; date unknown; pp. 893–908; Encyclopedia of Medical Devices and Instrumentation.

G. Garamy; *Engineering Aspects of Cryosurgical Instruments Employing Liquid Nitrogen*; 1967; pp. 283–308; International Ophthalmology Clinics.

J. Jones; *Mixed Gas Sorption Joule–Thomson Refrigerator*; May 1991; pp. i, 1–4; NASA Tech Brief.

J. Jones; *Sorption Refrigeration Research at JPL/NASA*; 1992; pp. 143–152; International Institute of Refrigeration.

J. Dow; *The Functional Anatomy of Urologic Cryosurgical Unit and Its Relation to the Technique, Complications, and Results of Cryosurgery of the Prostate*; Oct. 1969; pp. 572–577; The Journal of Urology, vol. 104.

J. Edwards; *A Simple Cryosurgical Instrument and Its Application in Ethiopia*; Nov. 1966; pp. 415–422, British Journal of Ophthalmology.

D. Ferris; *Cryosurgical Equipment: A Critical Review*; Feb. 1992; pp. 185–193; The Journal of Family Practice, vol. 35, No. 2.

W. Little; *Microminiature Refrigeration*; Jun. 1983, pp. 661–680; Rev. Sci. Instrum., vol. 55 No. 5.

W. Little; *Advances in Joule–Thomson Cooling*; 1990; pp. 1305–1314; Advances in Cryogenic Engineering, vol. 35.

S. Amolis; *The Joule–Thomson Cryoprobe*; Jan. 1967; pp. 201–207; Arch. Ophthal., vol. 78.

D. Friend; *Thermophysical Property Computer Packages from NIST*; 1992; pp. 13–18; ASME HTD vol. 225.

A. Gage; *Current Progress in Cryosurgery*; Mar. 1988; pp. 483–486; Cryobiology, vol. 25.

D. Hill; *Throttle Cycle Cooler Vibration Characterization*; 5 pages; date and place of publication unknown.

A. Khatri; *A Throttle Cycle Refrigerator Operating below 77K*; 8 pages; date and place of publication unknown.

G. Venkatarathnam; *Matrix Heat Exchangers and Their Applications in Cryogenic Systems*; Dec. 1989; pp. 907–918; Cryogenics, vol. 30.

R. Hubbell; *New Heat Transfer and Friction Factor Design Data for Perforated Plate Heat Exchangers*; 1988; pp. 383–390; Advanced Cryogenic Engineering, vol. 33.

H. Jichuan; *Heat Transfer Characteristics of a Perforated Plate*; Sep. 1990; pp. 318–322; Cryogenics, vol. 30.

G. Venkatarathnam; *Heat Transfer and Flow Friction Correlations in Perforated Plate Matrix Heat Exchangers*; Sep. 1990; pp. 313–317; Cryogenics, vol. 30.

Z. Chang; *Development of a High–Performance Multiprobe Cryosurgical Device*; Sep. 1994; pp. 383–390; Biomedical Instrumentation and Technology, vol. 28.

A. Hamilton; *An Electronic Cryoprobe for Cryosurgery Using Heat Pipes and Thermoelectric Coolers*; May 1993; pp. 104–109; Journal of Medical Engineering and Technology, vol. 17, No. 3.

Author unknown; *Technical Support Package on Mixed Gas Sorption Joule–Thomson Refrigerator*; May 1991; Jet Propulsion Lab.

A. Kleemenko; *One Flow Cascade Cycle(In Schemes of Natural Gas Liquefaction and Separation)*; 1959; pp. 34–39; Proceedings of International Congress of Refrigeration.

V. Kobryanskiy; *A Cryomedical Device Based On A Closed Cycle Joule–Thomson Cooling System*; Mar. 1978; pp. 71–72; place of publication unknown—Translated to English.

W. Little; *Development of a Low Cost, Cryogenic Refrigeration System for Cooling of Cryoelectronics*; 1994; pp. 1467–1474; Advances in Cryogenic Engineering, vol. 39.

W. Little; *Microminiature Refrigerators for Joule–Thomson Cooling of Electronic Chips and Devices*; 1990; pp. 1325–1333; Advances in Cryogenic Engineering, vol. 35.

W. Little; *Recent Developments in Joule–Thomson Cooling: Gases, Coolers and Compressors*; 9 pages; date and place of publication unknown.

W. Porter; *Processor Performance Enhancement Using CPU Sub–Cooling*; 1994; pp. 242–246; Proceedings of the International Electronic Packaging Conference.

Y. Rabin; *A Compact Cryosurgical Apparatus for Minimally Invasive Procedures*; May 1997; pp. 251–258; Biomedical Instrumentation and Technology.

S. Sood; *Prediction Methods for Vapor–Liquid Equilibria in Multi–Component Cryogenic Mixtures*; Jun. 1970; pp. 199–207; Cryogenics.

D. Torre; *Alternate Cryogens for Cryosurgery*; Jun. 1975; pp. 56–58; Journal of Dermatologic Surgery.

A. Gassanov; *Experience with the Development and Use of Cryogenic Surgical Equipment*; Sep. 1986; pp. 41–42; place of publication unknown—Translated to English.

A. Grokholski; *The Krioelektronika–1 Cryogenic Dental Unit*; Sep. 1981; pp. 16–20; Meditsinskaya Tekhnika—Translated to English.

J. Jones; *Cryogenic Mixed Fluid Application Study and Computer Code Development*; pp. i–iv, 1–18; date and place of publication unknown.

J. Pollard; *The Use of Crygoens in Glaucoma*; Nov. 1965; pp. 553–556; Southern Medical Journal.

S. Amoils; *A Cryosurgical System for Retinal Detachments and Tumours*; Feb. 1969; pp. 188–190; South African Medical Journal.

J. Addonizio; *Another Look at Cryoprostatectomy*; Dec. 1981; pp. 223–227; Cryobiology, vol. 19.

F. Brown; *Office Gynecologic Procedures*; Sep. 1986; pp. 493–511; Primary Care, vol. 13.

J. Baust; *Minimally Invasive Cryosurgery—Technological Advances*; Oct. 1996; pp. 373–384; Cryobiology, vol. 34.

Pittrof, R.; *Transcervical Endometrial Cryoablation (ECA) for Menorrhagia*; Jun. 1994; International Journal of Gynecology & Obstetrics 47 (1994); pp. 135–140.

\* cited by examiner

CRYOSURGICAL PROBE AND METHOD FOR UTERINE ABLATION

CROSS REFERENCE TO RELATED APPLICATIONS

This is a continuation-in-part patent application of U.S. patent application Ser. No. 08/774,148, filed on Dec. 26, 1996, now U.S. Pat. No. 5,910,104 and entitled "Cryosurgical Probe with Disposable Sheath."

STATEMENT REGARDING FEDERALLY SPONSORED RESEARCH OR DEVELOPMENT

Not Applicable

BACKGROUND OF THE INVENTION

1. Field of the Invention

The present invention is in the field of cryosurgical probes used for freezing and thereby destroying endometrial tissues within the uterus of a female patient.

2. Background Information

A Joule-Thomson refrigeration system operates by expanding a high pressure gas through an expansion element which incorporates some sort of a flow restriction. The flow restriction might be a small orifice, a narrow capillary tube, or some other sort of restricted passageway. Typically, the refrigeration system includes a source of high pressure gas, a heat exchanger, an expansion element, a heat transfer element, and various tubes or conduits to conduct the gas from one component to another. The high pressure gas passes through the heat exchanger to lower the gas temperature somewhat, then the gas temperature is further lowered in the expansion element, as isenthalpic expansion occurs. The expanded, cooled gas is exposed to the heat transfer element, where the gas absorbs heat which has been transferred from the environment. The operation of a Joule-Thomson refrigeration system can be severely affected by contaminants in the gas, such as water, oil, or particulates. Any such contaminant can easily block the flow restriction in the expansion element, because the flow restriction is typically very small.

Water and oil are particularly detrimental contaminants, because they will selectively collect at the flow restriction, where the majority of the cooling occurs. As the gas expands and cools, the temperature of entrained water and oil also lowers, resulting in the freezing or solidification of the water and oil. This solidification occurs exactly at the flow restriction, because that is where the cooling actually occurs. Water and oil, at least in trace amounts, are often found in ambient air, and they can consequently be introduced into the refrigeration system if any system joints are broken or any system parts are replaced.

Most Joule-Thomson systems are open loop, meaning that the gas is exhausted to the atmosphere after expansion and heat absorption. The source of the high pressure gas in such a system is usually a high pressure gas cylinder. As use proceeds, the amount of gas in the cylinder is depleted. An open loop system such as this can tolerate a certain amount of contamination, because the contaminants are exhausted from the system to the environment along with the gas, during use. If any contamination is introduced into the system during the replacement of parts, or when system joints are broken for other reasons, the contamination is largely flushed out as the gas is subsequently exhausted.

However, it is possible to operate a closed loop Joule-Thomson system, meaning that the gas is repressurized and circulated after expansion. After expansion in the expansion element, exposure to the heat transfer element, and absorption of heat, the low pressure gas is returned to a compressor which can be used to repressurize the gas. The repressurized gas is then circulated back through the heat exchanger and the expansion element. None of the gas is exhausted from the system. Therefore, any contaminants which enter the system are collected in the system, where they accumulate over a period of time. The level of contamination can eventually build up to a level where solidification of the water and oil will plug the expansion element. A method and apparatus have been developed for operating a micro-miniature mixed-gas Joule-Thomson refrigeration system, as disclosed in U.S. patent application Ser. No. 08/542,123, filed Oct. 12, 1995, and U.S. patent application Ser. No. 08/698,044, filed Aug. 15, 1996, which are incorporated herein for reference. If such a mixed-gas is used, especially in a miniature or micro-miniature refrigeration system, the introduction of air into the system alters the gas mixture ratios, and it can significantly detract from the cooling performance of the gas mixture.

For these reasons, closed loop Joule-Thomson systems are often permanently sealed, to prevent the introduction of contaminants. Replacement of parts, or other breaking of system joints, is not possible in a permanently sealed system. Some systems use self sealing couplings, which automatically close the system when they are broken apart. This automatic sealing limits the amount of leakage and contamination, but some contamination still occurs. Typically, the couplings used in a closed loop system are threaded fittings which are not designed for repetitive disconnection.

The contamination problem becomes more complicated in a closed loop mixed-gas Joule-Thomson refrigeration system which is used in a surgical device, such as a cryosurgical probe. Such a device will typically have a compressor hooked to the probe, with the probe consisting essentially of a handle, a cannula, and a cold tip. The heat exchanger is typically located in the handle, and the expansion element is typically located in the cold tip. The probe cannula or cold tip must be interchangeable with various shapes, such as flat, cylindrical, or sharp edged, to perform different functions. Further, the cold tip must be capable of being sterilized for use in a surgical application, to allow repeated use of the system on different patients.

Known cryosurgical probes are open loop systems for this reason. In an open loop system, the cannula or cold tip can be removed and sterilized or discarded. Introduction of contaminants into the refrigeration system during removal and replacement of the cannula or cold tip is not a significant problem in an open loop system, since the contaminants can be flushed from the system during exhaust of the gas. Open loop systems are wasteful and expensive to operate, because of the necessity of continually replacing the gas. Also, exhaust of the gas to the environment is not always environmentally safe. Closed loop systems are more economical and environmentally safe. If a known closed loop system were used in a surgical application, removal and replacement of the cannula or cold tip for sterilization purposes would introduce contaminants into the system, ultimately resulting in blockage of the expansion element. A closed loop surgical system could theoretically be provided with self sealing couplings, but contamination would still build up over a period of time. Further, self sealing couplings incorporate O-rings and precision parts. Sterilization of the cannula or cold tip would inevitably expose the O-rings and precision parts to high temperatures and harsh chemicals, ultimately resulting in degradation of the sealing ability of the couplings.

Use of disposable replacement cannulas or cold tips would not solve this dilemma. First, even if the replaceable parts are discarded and replaced with new, sterile parts, repetitive disconnections are required, ultimately resulting in the buildup of contaminants. Second, most disposable parts are constructed of plastic, for reasons of economy. Plastics typically contain trace amounts of water. If a plastic part is exposed to the gas in a refrigeration system, the water can eventually leech out of the plastic and contaminate the gas in the system. Third, self sealing fittings typically add size, weight, and significant cost to a device, making them undesirable for use in a disposable device. Fourth, each time a disposable element, such as a cannula or cold tip, is discarded, the refrigerant gas contained within the disposable element is lost. This requires replacement of the gas to avoid degradation of the cooling performance of the system. Evacuation of gas from the disposable component, or use of replacement components precharged with gas, would significantly add to the complexity and cost of the system.

Further, a typical cryosurgical probe will have one or more auxiliary instruments near the cold tip, for use in conjunction with the cold tip, such as temperature sensors, heaters, ultrasound transducers, optical elements, and fluid ports for irrigation and aspiration. If a reusable probe is employed, repetitive sterilization of these auxiliary instruments can degrade their performance. The ideal practice would be to incorporate these auxiliary instruments into a disposable element.

Finally, it is desirable to insulate the shaft of a cryosurgical probe, to prevent freezing of tissue at undesired sites along the probe when the probe is inserted into a body cavity or organ. One effective means of insulation would be to provide a vacuum space along the probe shaft. However, the level of the vacuum maintained in such a space can degrade over time, because of the outgassing of metals, plastics, and braze joints. This outgassing increases during sterilization procedures in which heat is applied to the probe. Therefore, it would be desirable to incorporate the vacuum insulation space into a disposable element. The disposable element would only be sterilized once, and the disposable element can then be economically discarded, minimizing the amount of vacuum degradation.

Further, it has been found that certain methods of use of a cryosurgical probe can be more effective than others. In the clinical use of a cryosurgical probe, important features of the method are the exact positioning of the probe in-vivo, and the sequencing of the various functions of which the probe may be capable. While the temperature and flow rate of mixed gas maintained at the probe tip establish the size and temperature gradient of the ice ball formed, which determines the total volume of tissue frozen and destroyed, probe positioning during tissue freezing determines the total effective area coverage. Depending upon the particular shape and size of the tissue area being treated, repositioning may be required to achieve optimal area coverage and ensure complete tissue ablation. Repositioning technique becomes an important feature in ensuring complete tissue area coverage. This is particularly true in the cryoablation of tissue in the endometrium of the uterus.

BRIEF SUMMARY OF THE INVENTION

The present invention is a method for ablation of endometrial tissue and a cryosurgical probe for use in the method, which can incorporate a disposable, sterilizable sheath, a heater, and a saline irrigation flow path. The sheath is sufficiently flexible to be slipped over the probe, thereby separating the probe from the environment and allowing use of the probe in a surgical application. The sheath has a grip which fits snugly over the handle of the cryosurgical probe, and an extendible shroud attached to the proximal end of the grip. The shroud can be longitudinally extended to cover the refrigerant tubing and instrumentation cables which are attached to the handle, thereby providing a sterile barrier for these components.

The sheath also has a hollow multi-lumen catheter attached to the distal portion of the grip, with at least one lumen being shaped and sized to fit snugly over the cannula of the cryosurgical probe. The catheter is not thermally conductive, so it assists in preventing transfer of heat from the ambient to the gas mixture, and preventing the freezing of tissues at undesired locations along the catheter. Thermal conductivity of the catheter can be reduced by the provision of insulation, such as a vacuum space, along the sides of the catheter. A thermally conductive segment is attached to the distal end of the multi-lumen catheter, in the form of a metal cap or tip. The metal tip can be round, flat, sharp, or any other shape suitable for the cryosurgical operation being performed. The thermally conductive cap or tip fits snugly over the cold tip on the probe, and it efficiently transfers heat from the target tissue to the cold tip, which in turn transfers heat to the expanded gas mixture. Various forms of auxiliary instrumentation can be mounted on the catheter or conductive tip, such as a temperature sensor, a heater, a tissue impedance measuring component, an ultrasonic transducer, or an optical element of a viewing, illumination, or laser system. Connections between the instrumentation near the distal end of the catheter and the probe are made via a plurality of lumens passing longitudinally through the wall of the catheter. Fluid passageways can also be included in the catheter, and they can be connected to fluid sources connected to, or mounted on the sheath, such as a saline reservoir mounted on the grip of the sheath. These fluid passageways can be utilized as explained below to supply irrigating fluid, such as a saline solution, to the vicinity of the cold tip, to aid in releasing the cold tip from the ice ball when repositioning of the probe is necessary. As an alternative to provision of fluid passageways in the sterile sheath, such passageways can be provided in the probe itself, without departing from the spirit of the present invention.

The method of the present invention also incorporates the placement of the probe at certain locations within the uterus, depending upon the size of the uterus, with certain sequencing of the functions of the probe to insure complete freezing of the target tissue.

The novel features of this invention, as well as the invention itself, will be best understood from the attached drawings, taken along with the following description, in which similar reference characters refer to similar parts, and in which:

DETAILED DESCRIPTION OF THE INVENTION

Figures 1, 2A:
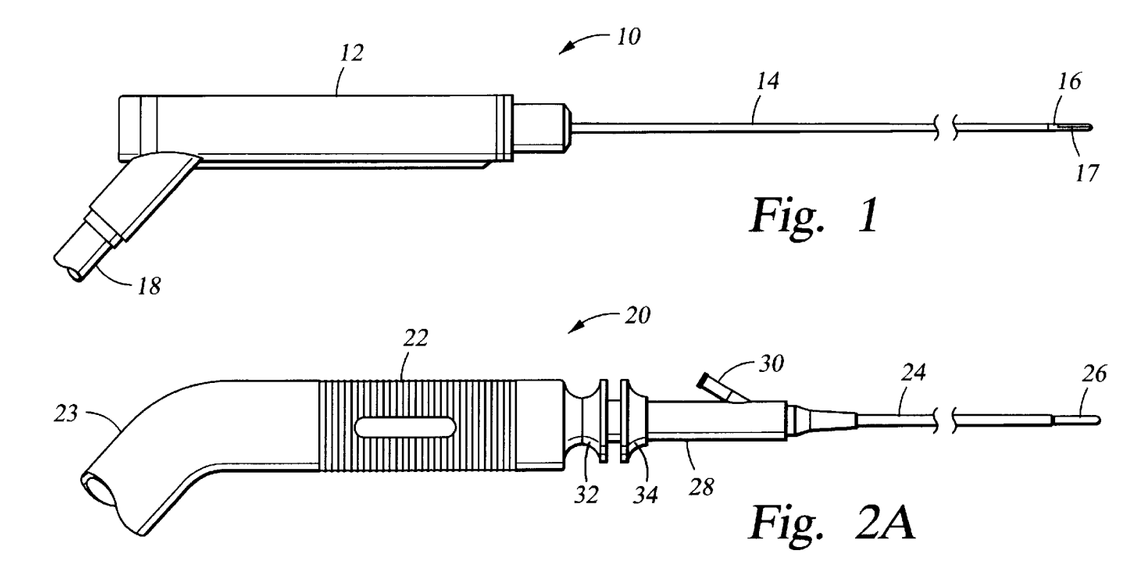
FIG. 1 is an elevation view of a cryosurgical probe of the type which might be used in the present invention.
FIG. 2A is an elevation view of a disposable sheath.

The present invention addresses the use of a cryosurgical probe in performing a new procedure for cryoablation of endometrial tissue in the uterus of a female patient. Such a cryosurgical probe 10 is shown in FIG. 1. The probe 10 consists mainly of a handle 12, a hollow tubular cannula 14, and a cold tip 16. The handle 12 can be metallic, to facilitate effective sealing. The handle can have end caps vacuum brazed to the handle cylinder, to hold a vacuum inside the handle 12, thereby providing insulation. Alternatively, the handle 12 could be packed with insulating material, such as aerogel. Several components of the refrigeration system, such as a heat exchanger, can be housed within the handle 12, along with various auxiliary instrumentation to support items such as temperature sensors, heaters, illumination optics, viewing optics, laser optics, and ultrasonic transducers. An umbilical cord 18 extending from the proximal portion of the handle 12 can contain tubing for the refrigeration system, power cables for the electrical components, or fiber optical cables to support the illumination, viewing, and laser components.

Other components of the refrigeration system, such as a high pressure conduit to transport a high pressure gas mixture from the probe handle 12 to the cold tip 16, and a low pressure conduit to return the expanded gas mixture from the cold tip 16 to the probe handle 12, can be housed in the hollow cannula 14. Still other components of the refrigeration system, such as a Joule-Thomson expansion element, can be housed in the cold tip 16. The hollow cannula 14 is usually designed to minimize heat transfer from the surrounding tissues to the cryogenic gas mixture. It can be formed of a thermally resistive material, such as a rigid plastic, or it can be formed of a metal, with insulation applied internally or externally to inhibit heat transfer. The cannula 14 can be a rigid tube as shown, or it can be more flexible and shaped differently, depending upon the application. The cold tip 16 is a heat transfer element designed to maximize heat transfer from the target tissues to the expanded gas mixture. It can be formed of a thermally conductive material, such as a metal, preferably silver. The cold tip 16 can be a cap shaped element on the distal end of the cannula 14 as shown, or it can have another shape and be placed elsewhere on the cannula 14, depending upon the application. A plurality of grooves 17 are formed in the cold tip 16 to allow the flow of thermal grease as the cold tip 16 is fitted inside the disposable sheath. Since the cryosurgical probe 10 is used with a closed loop refrigeration system, it will necessarily be sealed to prevent contamination. It may have breakable joints which allow for replacement of parts, but any such joints will necessarily have sealing components which are not suitable for normal sterilization procedures.

FIG. 2A shows a disposable, sterilizable sheath 20 which can be disposed over, and thereby incorporated into, the probe 10, to allow use of the probe 10 in a sterile environment without degradation of the effectiveness of the probe 10. Since the sheath 20 can be sterilized easily, and since it is constructed cheaply enough to be disposable, the probe 10 need not be sterilized. The disposable sheath 20 includes a grip 22 which fits over the probe handle 12, preferably with corrugations or other surface features to provide a secure feel for the surgeon. An extendible shroud 23 is attached to or formed on the proximal portion of the grip 22. The shroud 23 is shown in FIG. 2A in the unfurled, or extended, condition, covering the umbilical cord 18 and the proximal portion of the probe handle 12. The grip 22 and the shroud 23 are constructed of a thermally nonconductive material, such as a plastic. They should have some flexibility to allow them to fit over the probe handle 12 and the umbilical cord 18. The sheath 20 also includes a hollow tubular catheter 24 extending distally. The hollow catheter 24 is shaped and sized to cover the cannula portion 14 of the cryosurgical probe 10, preferably fitting tightly over the probe cannula 14 to avoid interference with use of the probe 10 in a surgical environment. The hollow catheter 24 is constructed of a thermally resistive material, such as a plastic, to further inhibit heat transfer from the surrounding tissues to the probe cannula 14.

Figure 14:
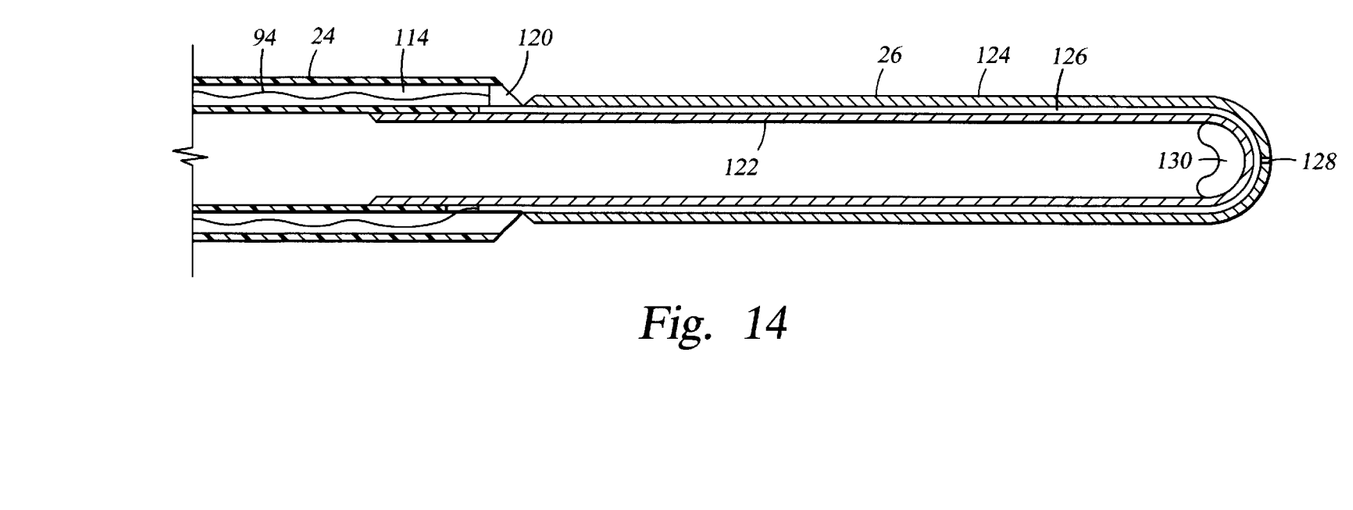
FIG. 14 is a longitudinal section view of the distal end of the catheter of the disposable sheath.

Attached to the distal end of the hollow catheter 24 is a thermally conductive segment, such as a cap shaped tip 26. The sheath tip 26 is shaped and sized to fit snugly over the probe cold tip 16, to maximize the transfer of heat through the sheath tip 26 to the probe cold tip 16. A thermal grease 130 can be placed between the probe cold tip 16 and the sheath tip 26, as shown in FIG. 14, to insure efficient heat transfer from the sheath tip 26 to the probe cold tip 16. The sheath tip 26 can be a cap shaped element on the distal end of the catheter 24 as shown, or it can be a thermally conductive segment shaped and located otherwise, to match the configuration and location of the probe cold tip 16. The thermally conductive segment of the sheath, such as sheath tip 26, must be constructed of a material which will readily transfer heat, such as a metal. All of the components of the sheath 20 are attached together in a sealing relationship, so that when the sheath 20 is sterile, it covers the probe 10 in a sterile envelope, rendering the probe 10 suitable for use in a surgical environment. Various auxiliary instruments for use in conjunction with cryosurgery can be mounted in the hollow catheter 24 or the sheath tip 26, as will be explained below. These instruments can include temperature sensors, heaters, viewing optics, illumination optics, laser optics, and ultrasonic transducers. Controls for operating these instruments, or devices for displaying readings from these instruments, can be mounted in the probe handle 12 or elsewhere, for ease of observation and use by the surgeon. Connections between the instrumentation near the sheath tip 26 and the control devices in the probe handle 12 or proximal to the handle 12 can be carried by the hollow catheter 24 as will be explained.

The sheath 20 can also include a substantially rigid connector body 28, which performs several functions. The connector body 28 provides a means for connecting the hollow catheter 24 to the grip 22. It can also provide a means for latching the sheath 20 to the probe 10. Further, the connector body 28 can provide a mounting location for connectors, such as electrical contacts or optical elements, to connect auxiliary instrumentation near the sheath tip 26 to the probe handle 12.

Figure 2B:
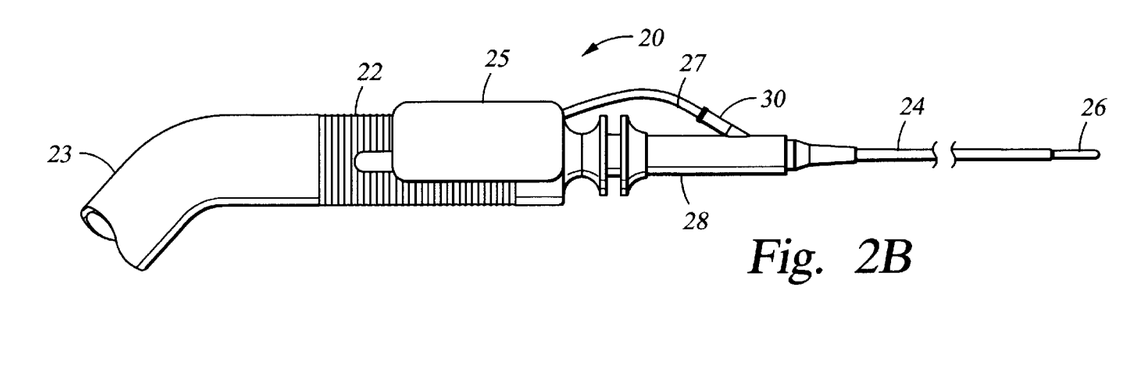
FIG. 2B is an elevation view of an alternative embodiment of the disposable sheath.
Figure 2C:
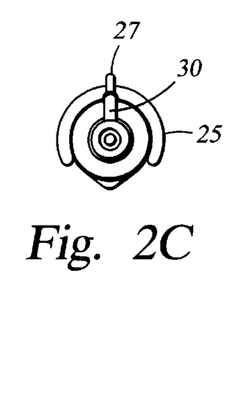
FIG. 2C is a distal end view of the alternative embodiment of the disposable sheath shown in FIG. 2B.

Finally, the connector body 28 can provide a mounting location for a port or fitting 30, such as a luer fitting, which can be used to provide fluid flow to or from the area adjacent the sheath tip 26. Fluid flow to the area can be required in some applications where fluid such as a saline solution must be injected into a body cavity having a small opening. An example of such an application is use of the probe cannula 14 in the uterus for endometrial ablation. In this application, it can be useful to inject a saline solution adjacent the cold tip to partially thaw the proximal portion of the ice ball and release the cold tip from the ice ball. This is also helpful in thawing the proximal portion of the ice ball, thereby allowing movement of the probe to a new position in the uterus. Fluid flow to the area around the tip 26, such as a saline solution or another fluid suitable for irrigation of the area, can be provided by a syringe attached to the fitting 30. Alternatively, as shown in FIGS. 2B and 2C, a pliable saline reservoir 25 can be mounted on the grip 22 and connected to the fitting 30 by a tube 27. Squeezing or depressing the saline reservoir 25 can inject saline solution into the fitting 30. The injected fluid can be retained in the body cavity by sliding a plug (not shown) over the cannula 14 and the catheter 24 to fit snugly between the catheter 24 and the opening of the body cavity. Similarly, a balloon (not shown) can be inflated around the catheter 24 to seal against the cavity opening. Fluid flow from the area around the tip 26 can be achieved by connecting a vacuum source to the fitting 30. Fluid flow can pass between the tip area and the fitting 30 via the hollow catheter 24, as will be explained below.

FIG. 2A also shows the finger stop 32 formed on the distal portion of the sheath grip 22, and the finger slide 34 formed on the proximal portion of the connector body 28. As will be shown below, the finger slide 34 can be pulled toward the finger stop 32 to unlatch the connector body 28 from the probe handle 12.

Figure 3:
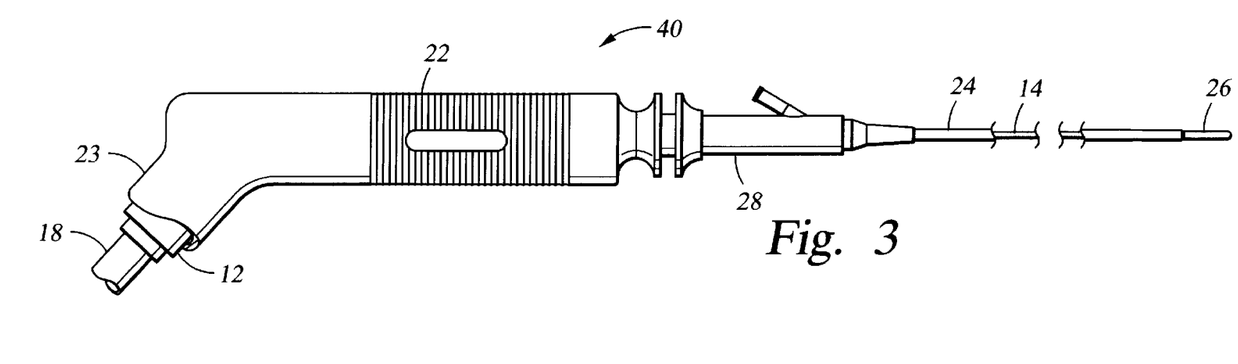
FIG. 3 is an elevation view of a disposable sheath in place over a cryosurgical probe.

FIG. 3 shows the combined cryosurgical instrument 40 of the present invention, consisting of the sterile sheath 20 disposed over the probe 10 as a sterile cover, having a thermally conductive segment for effectively transferring heat from the target tissue to the cold tip 16 of the probe 10. It should be noted that the shroud 23 of the sheath 20 is sufficiently flexible to stretch over the proximal end of the probe handle 12 and the umbilical cord 18.

Figure 4:
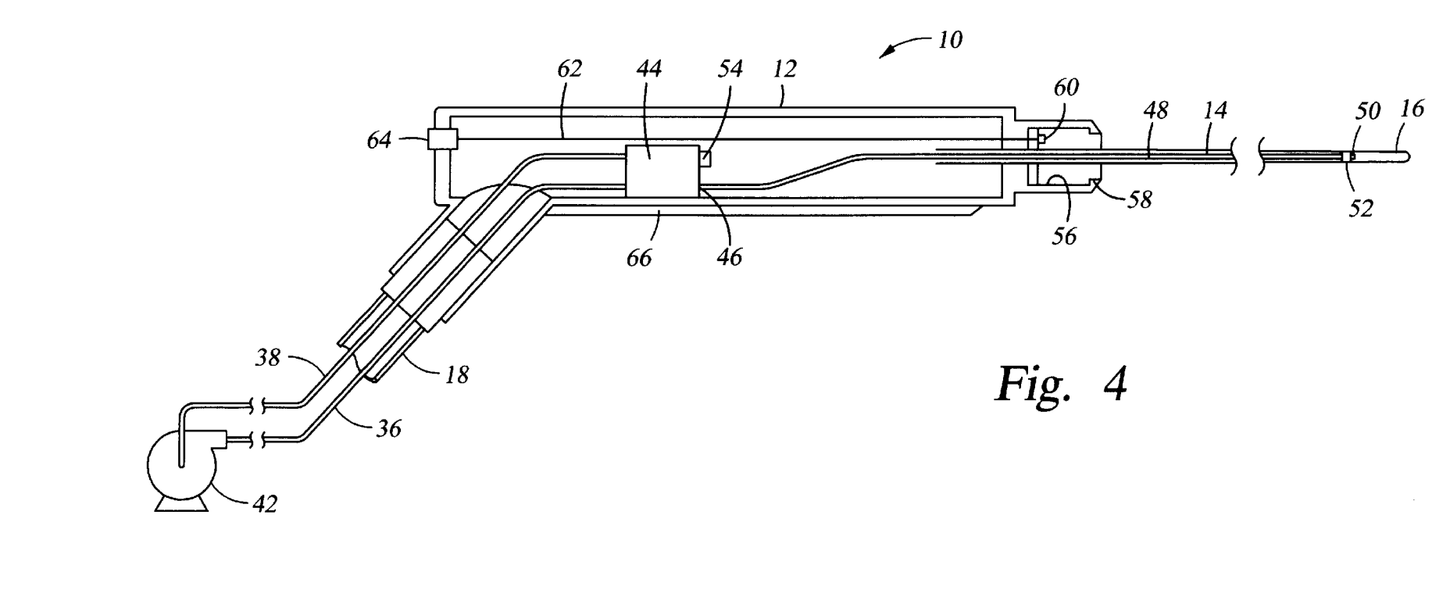
FIG. 4 is a schematic view of a cryosurgical probe as shown in FIG. 1.

FIG. 4 is a schematic drawing of the cryosurgical probe 10, in the style of a longitudinal section view, to illustrate the components and functions of the typical probe 10 which can be incorporated into the present invention. A high pressure gas tube 36 provides a warm high pressure gas mixture to the refrigeration components in the probe 10, and a low pressure gas tube 38 receives the cool low pressure gas mixture returning from the probe 10. The high pressure and low pressure gas tubing 36, 38 is connected to the outlet and inlet, respectively, of a gas compressor 42. The high pressure tube 36 is also connected to a high pressure passageway through a precooling heat exchanger 44, and the low pressure tube 38 is connected to a low pressure passageway through the heat exchanger 44. The heat exchanger 44 precools the warm high pressure gas mixture by heat exchange with the cool low pressure expanded gas mixture, before the high pressure gas is expanded at the cold tip 16.

A high pressure outlet 46 of the heat exchanger 44 is connected to a high pressure conduit 48 which passes through the hollow cannula 14 to the cold tip 16. At the distal end of the high pressure conduit 48 is a Joule-Thomson expansion element 50, located in, or immediately adjacent to, the cold tip 16. High pressure cryogenic gas mixture passing through the high pressure conduit 48 is isenthalpically expanded by the expansion element 50, to significantly lower the temperature of the gas mixture. The colder, low pressure gas mixture is then exposed to the cold tip 16, to cool the target tissue via the thermally conductive sheath tip 26. A separator plate 52 isolates the low pressure region of the cold tip 16 from the probe cannula 14. Low pressure gas mixture passes back through openings in the separator plate 52 to return via the probe cannula 14 to the low pressure inlet 54 of the heat exchanger 44. The flow of the low pressure gas mixture back through the cannula 14 can actually be via a low pressure conduit not shown in FIG. 4.

A female connector fitting 56 is provided in the distal portion of the probe handle 12, to provide for a mating location between the probe 10 and the sheath 20. An inwardly projecting latching flange 58 can be provided around the outer perimeter of the female connector 56. One or more connector elements 60 can be provided within the female connector 56 for mating with auxiliary instrumentation carried by the sheath 20. The connector element 60 can be an electrical contact for use with auxiliary instrumentation such as a temperature sensor, a heater, or an ultrasonic transducer. Similarly, the connector element 60 can be an optical element for use with auxiliary instrumentation such as viewing optics, illumination optics, or laser optics. The connector element 60 is connected by way of an instrumentation conductor 62 to a display or control device 64. The instrumentation conductor 62 can be an electrical conductor or an optical fiber bundle, as appropriate. Only one set of connector element 60, conductor 62 and display or control device 64 is shown, for the sake of simplicity, but it should be understood that a plurality of such systems could be used in any given cryosurgical instrument 40. Further, it should be understood that the display or control device 64 could be located remotely from the instrument 40, such as would be appropriate for a video optical viewing system. An alignment rib 66 can be formed on the perimeter of the probe handle 12, to assist in alignment of the probe handle 12 with the sheath grip 22.

Figure 5:
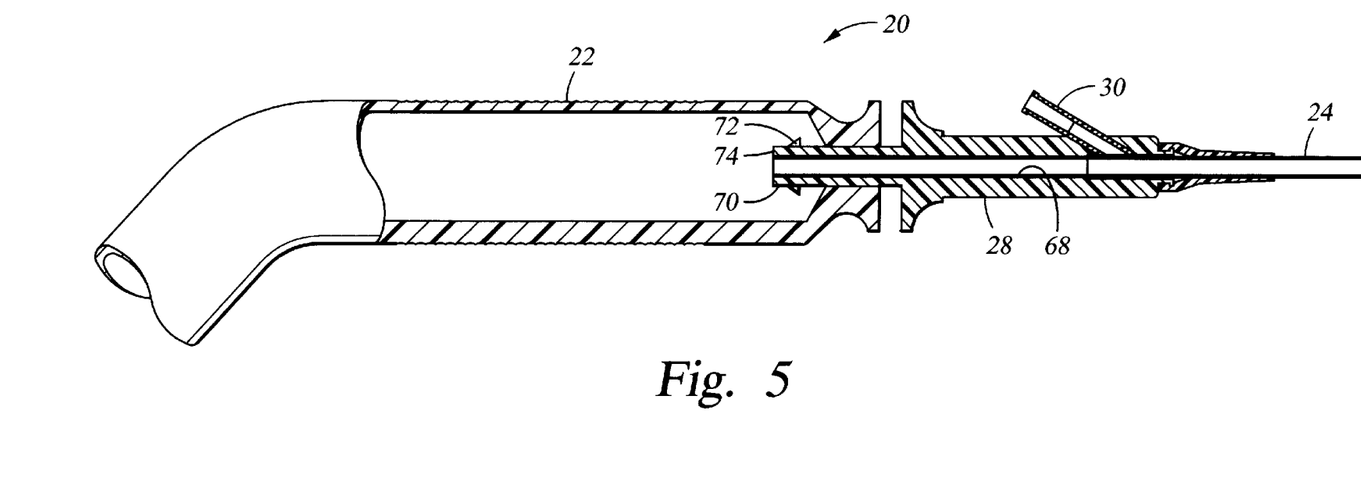
FIG. 5 is a section view of the proximal portion of the disposable sheath as shown in FIG. 2A.
Figure 6:
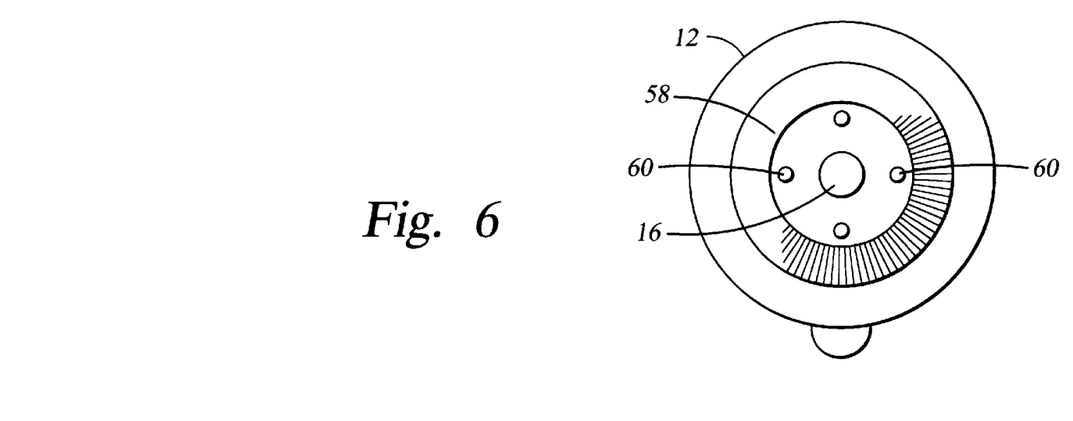
FIG. 6 is a distal end view of the cryosurgical probe as shown in FIG. 1.

FIG. 5 shows that the connector body 28 has a longitudinal bore 68 therethrough, to allow the passage of the probe cannula 14. The fitting 30 is in fluid flow communication with the bore 68, to provide fluid flow to the exterior of the hollow catheter 24, which extends into the bore 68. A male connector fitting 70 is provided on the proximal portion of the connector body 28 to mate with the female connector fitting 56 in the distal portion of the probe handle 12. A releasable latch 72 is provided on the male connector fitting 70, to engage the latching flange 58. One or more connector elements 74 are also provided on the male connector fitting 70 to engage the connector elements 60 within the female connector fitting 56 in the probe handle 12. Connection of the connector element 74 to the auxiliary instrumentation, and connection of the fluid flow path from the fitting 30 to the hollow catheter 24 are shown better in a later Figure. FIG. 6 is an end view of the probe handle 12, showing the interior of the female connector fitting 56. A plurality of connector elements 60 are shown arranged in a circle within the female fitting 56.

Figure 7:
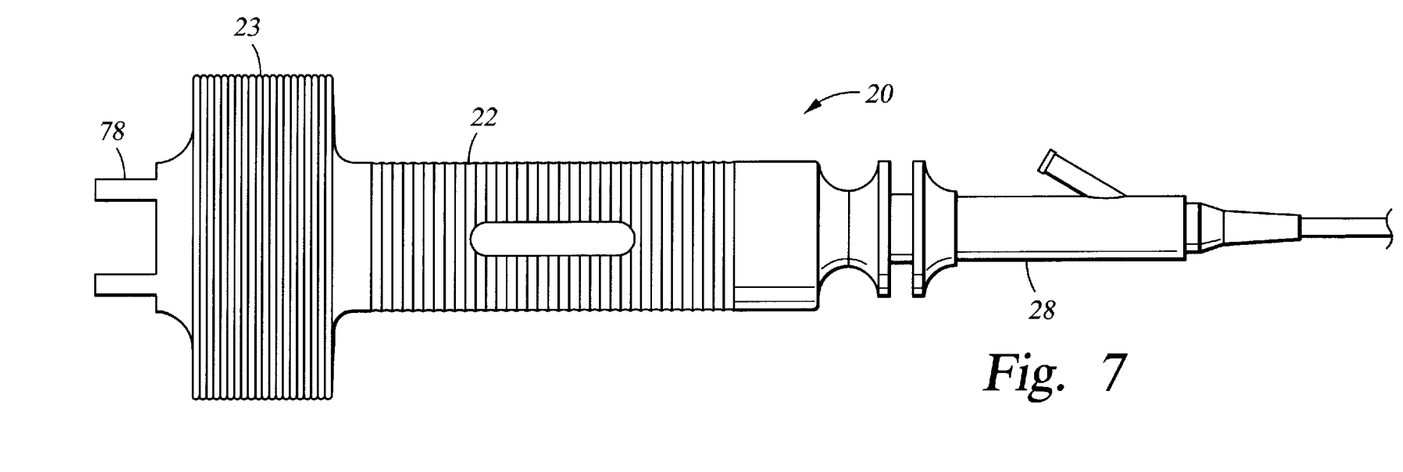
FIG. 7 is an elevation view of the proximal portion of the disposable sheath of FIG. 1, with the shroud furled.
Figure 8:
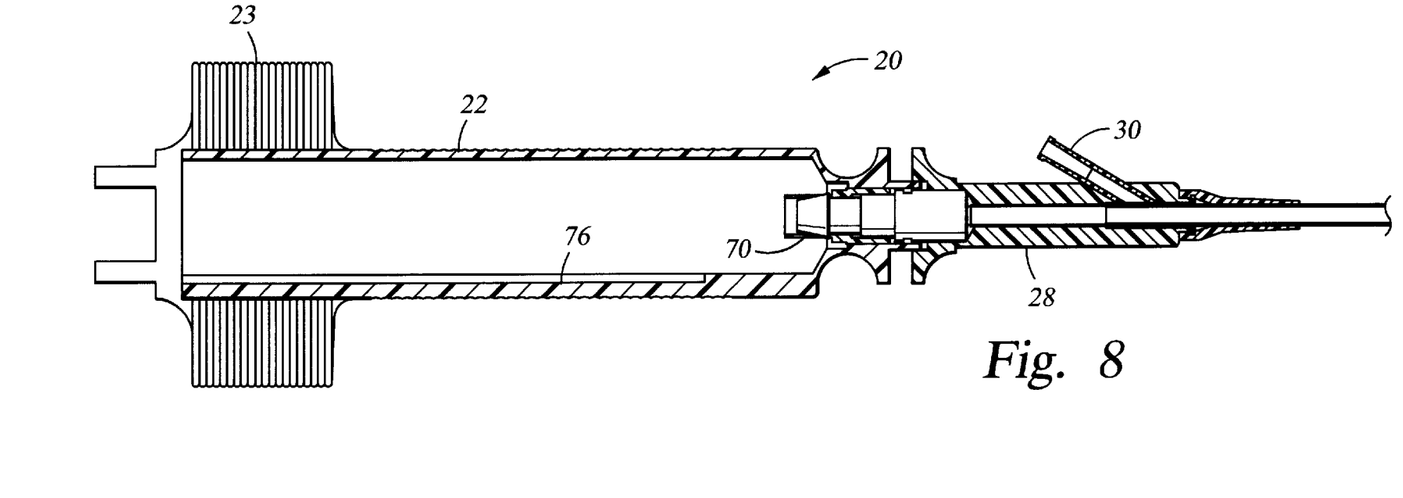
FIG. 8 is a section view of the proximal portion of the disposable sheath of FIG. 7, with the shroud furled.

FIG. 7 shows the sheath 20 with the shroud 23 in the furled, or contracted, condition. The sheath would normally be shipped and stored in this condition until disposition over a cryosurgical probe 10. Tabs 78 are provided on the proximal end of the shroud 23 to assist in pulling the shroud 23 over the probe handle 12 and the umbilical cord 18. FIG. 8 is a section view showing more detail of one embodiment of the sheath 20. An alignment groove 76 is shown in the inner bore of the sheath grip 22, to mate with the alignment rib 66 on the exterior of the probe handle 12. It can be seen that the connector body 28 can be constructed as a multi-piece assembly.

Figure 9:
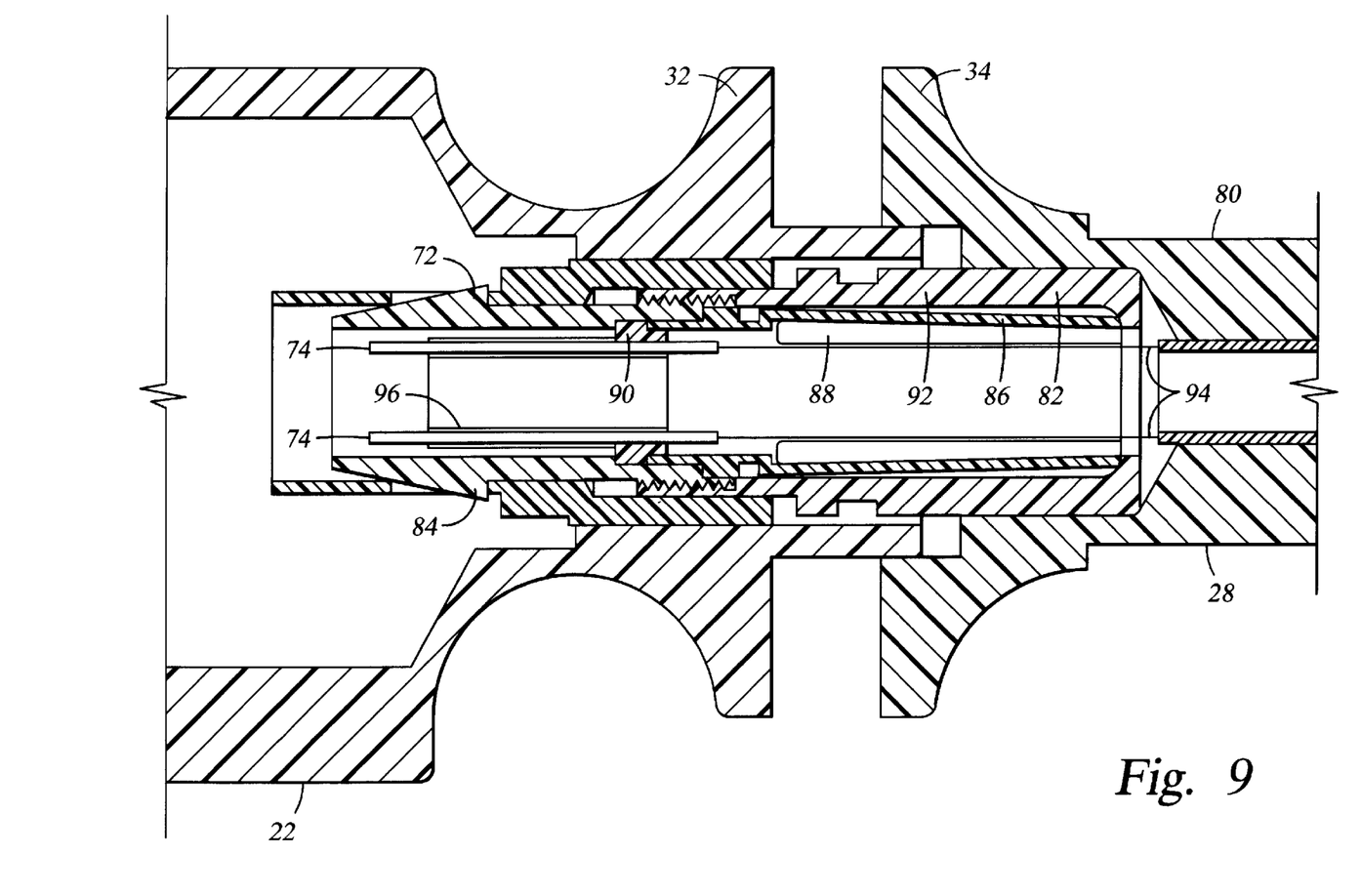
FIG. 9 is a longitudinal section view of the proximal portion of the connector body of the disposable sheath.

FIG. 9 shows more detail of one embodiment of the connector body 28 and its connection to the sheath grip 22. The connector body 28 comprises essentially a distal section 80, an intermediate section 82, and a proximal section 84. The distal section 80 includes the finger slide 34, and the distal portion of the distal section 80 is attached to the hollow catheter 24. The intermediate section 82 is mounted within the proximal portion of the distal section 80, and it provides a means of connecting the distal section 80 to the instrumentation connectors 74 and to the releasable latch 72. The intermediate section 82 can consist of a barrel 92 as shown, threaded to the latch 72. A collet 86 is captured between the barrel 92 and the latch 72. The collet 86 is attached to a sleeve 90 which is in turn attached to a connector fixture 96. Instrumentation conductors 94 are connected to the instrumentation connectors 74. The instrumentation conductors 94 pass through or alongside the longitudinal bore 68 to the catheter 24.

Figure 10:
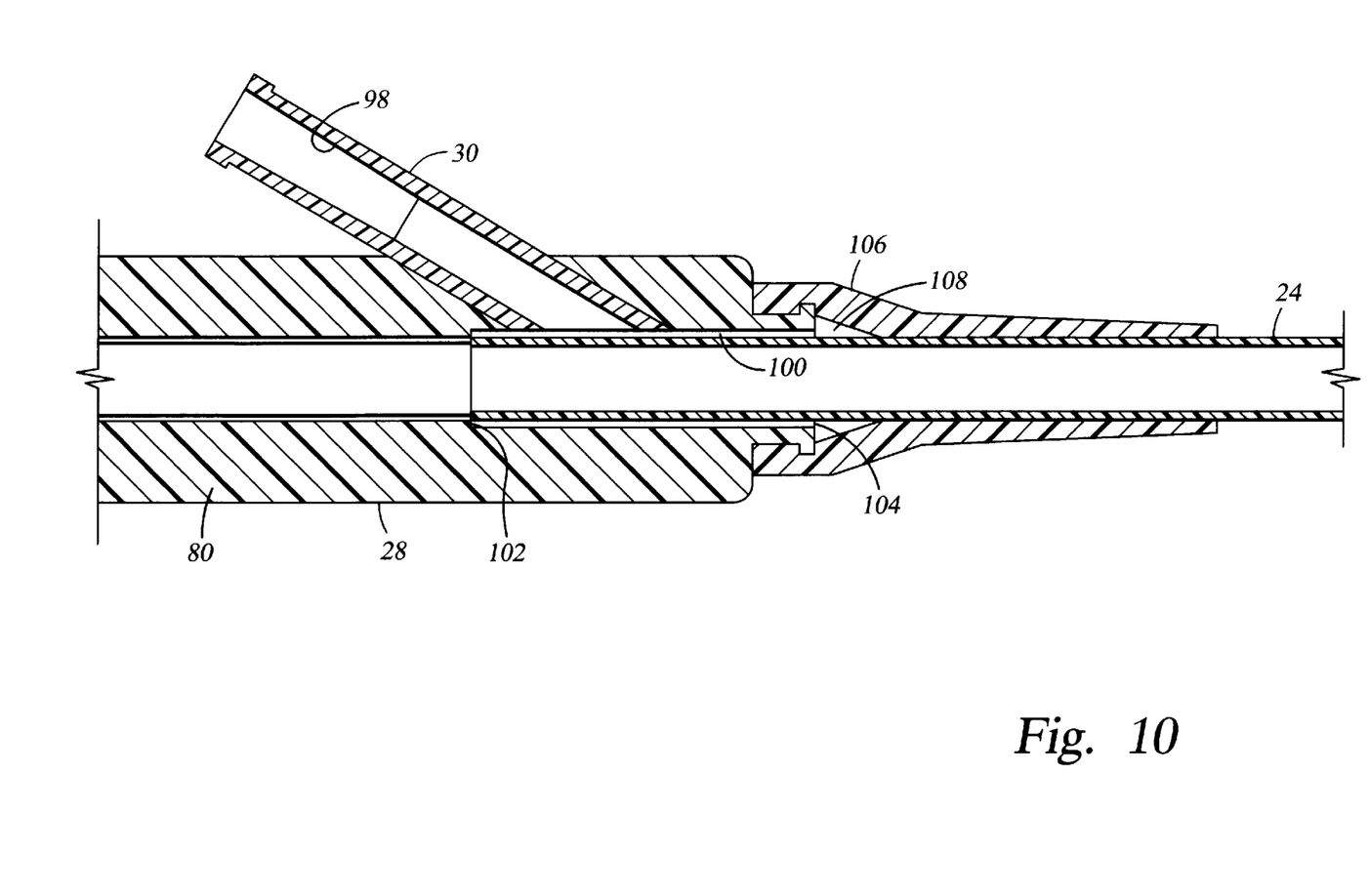
FIG. 10 is a longitudinal section view of the distal portion of the connector body of the disposable sheath.

FIG. 10 shows more detail of one embodiment of the distal portion of the distal section 80 of the connector body 28. The distal end of the longitudinal bore 68 terminates in a fluid bore 100, which is in fluid flow communication with an internal bore 98 of the fitting 30. The proximal portion of the hollow catheter 24 extends into the fluid bore 100, with the diameter of the fluid bore 100 being larger than the outer diameter of the catheter 24. This leaves a fluid flow space surrounding the catheter 24 in the fluid bore 100. The proximal end 102 of the fluid bore 100 can be terminated by a shoulder in the longitudinal bore 68. Conversely, the proximal end 102 of the fluid bore 100 can be terminated by an epoxy seal. The probe cannula 14 can fit snugly within the longitudinal bore 68. The distal end of the connector body 28 can be fitted with a strain relief collar 106 to fasten the catheter 24 to the connector body 28. A space 108 within the collar 106 can be filled with epoxy to terminate the distal end of the fluid bore 100.

Figures 11, 12A, 12B:
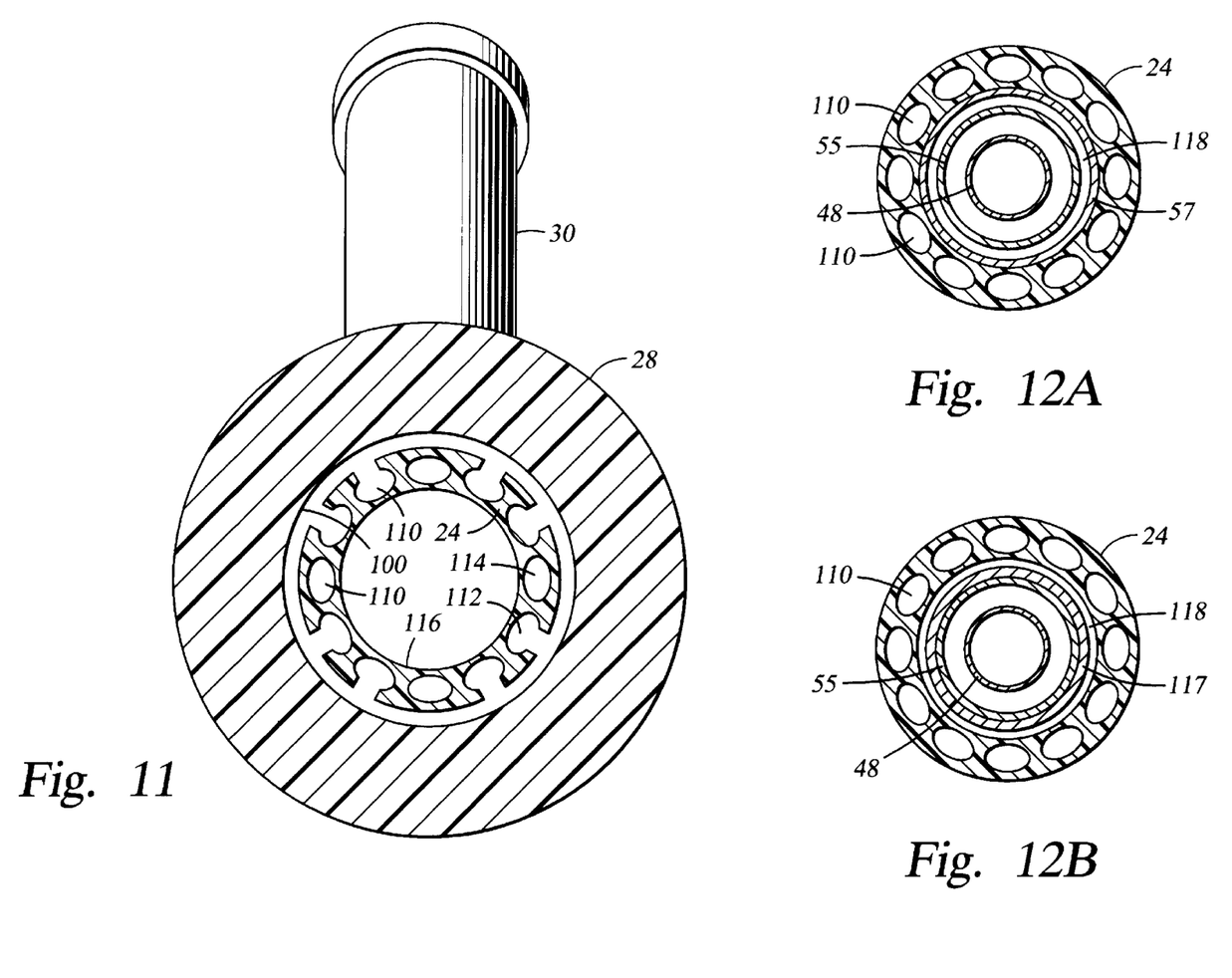
FIG. 11 is a transverse section view of the distal portion of the connector body of the disposable sheath.
FIG. 12A is a transverse section view of the catheter of the disposable sheath installed on the cannula of the cryosurgical probe.
FIG. 12B is a transverse section view of an alternate embodiment of the catheter of the disposable sheath, including a vacuum jacket, installed on the cryosurgical probe.

FIG. 11 shows a section view of the distal portion of the connector body 28 and the proximal portion of the hollow catheter 24. In this view, it can be seen that the catheter 24 is a multi-lumen catheter. A plurality of lumens 110 pass longitudinally through the wall of the catheter 24. Some of the lumens 110 are used to conduct fluid flow, as shown at 112, and other lumens are used to conduct auxiliary instrumentation signals, as shown at 114. Within the fluid bore 100 only, the fluid lumens 112 are open to the exterior of the catheter 24, while the fluid lumens 112 along the remainder of the length of the catheter 24 are not open to the exterior. The instrumentation lumens 114 are closed to the exterior throughout the length of the catheter 24. Since the fluid lumens 112 are open to the exterior within the fluid bore 100, fluid can flow from the fitting 30 into the wall of the catheter 24, or out of the wall of the catheter 24 to the fitting 30. A central bore 116 passes through the catheter 24 to accommodate the probe cannula 14.

FIG. 12A shows a transverse section view of the catheter 24 and the probe cannula 14, forward of the connector body 28. The cannula 14 incorporates a set of three coaxial stainless steel tubes 48,55,57, with the outer tube 57 fitting substantially snugly within the catheter 24. It can be seen that a vacuum or insulation space 118 is formed between the outer tube 57 and a low pressure conduit 55. The low pressure conduit 55 leads to the low pressure inlet 54 of the heat exchanger 44. The high pressure conduit 48 lies within the low pressure conduit 55.

FIG. 12B shows a transverse section view of an alternate embodiment of the catheter 24 and the probe cannula 14, forward of the connector body 28. The cannula 14 incorporates a set of two coaxial stainless steel tubes 48,55, with the outer tube 55 fitting substantially snugly within an inner tube 117 in the catheter 24. It can be seen that a vacuum jacket or insulation space 118 is formed within the catheter 24, between the inner tube 117 and the catheter 24. Here as before, the low pressure conduit 55 leads to the low pressure inlet 54 of the heat exchanger 44. The high pressure conduit 48 lies within the low pressure conduit 55.

Figure 13:
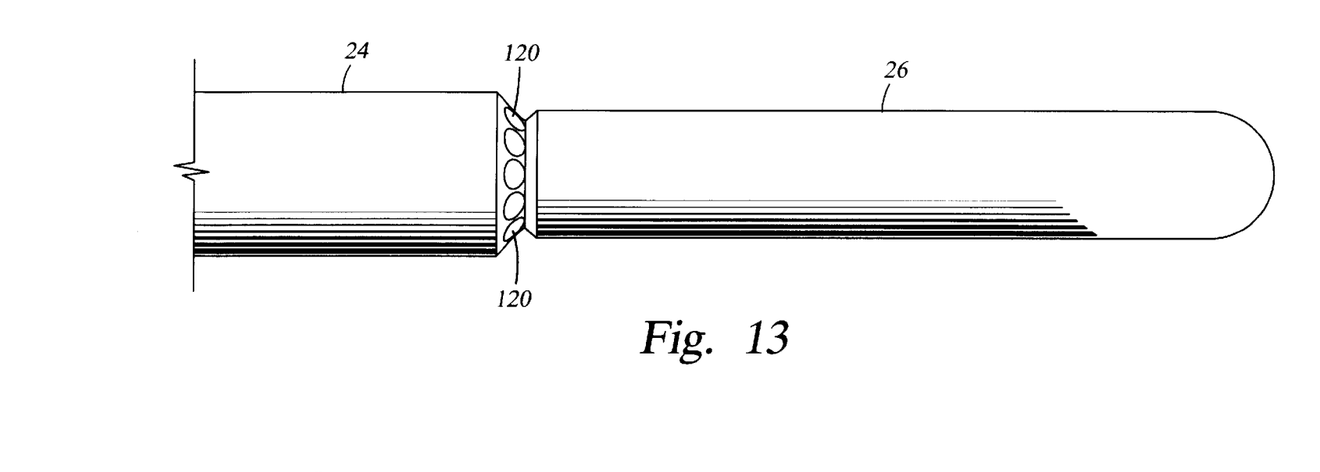
FIG. 13 is an elevation view of the distal end of the catheter of the disposable sheath.

FIG. 13 shows an elevation view of the distal end of the hollow catheter 24 and the sheath tip 26. A plurality of ports 120 in the lumens 110 are formed in the distal end of the catheter 24. Some of the ports 120 are for fluid flow to or from the area adjacent the sheath tip 26. Other ports 120 are for optical elements to support viewing, illumination, or laser systems. Still other ports 120 could be used as connection terminals for electrical connection to a temperature sensor, heater, or ultrasonic transducer in the sheath tip 26.

FIG. 14 shows a longitudinal section of the distal portion of the catheter 24 and the sheath tip 26. The auxiliary instrumentation conductor 94 passes through a lumen 114 to the distal end of the catheter 24, at which point it connects to an optical element in the port 120, or to an auxiliary instrument 126 in the sheath tip 26. The auxiliary instrument 126 could be a temperature sensor, a heater, a tissue impedance measuring component, or an integrated component for performing two or more of the temperature sensing, impedance measuring, and heating functions. For example, the instrument 126 could be a combination heater and resistance temperature detector (RTD) constructed of foil laminated between very thin (0.003 in.) sheets of polyimide film. Further, the auxiliary instrument could be an ultrasonic transducer. Those auxiliary instruments 126 which are in the sheath tip 26 can be sandwiched between an inner thermally conductive layer 122 and an outer thermally conductive layer 124. The inner conductive layer 122 can be made of copper, and the outer conductive layer 124 can be made of stainless steel. If desired, epoxy can be injected between the instrument 126 and the conductive layers 122, 124. An epoxy bleed hole 128 in the outer layer 124 is provided for this purpose. If insulating layers are placed between the instrument 126 and the inner and outer layers 122, 124, the insulating layers must be sufficiently thin to allow heat transfer therethrough. A thermally conducting grease 130 can be provided within the sheath tip 26 to maximize the thermal contact between the probe tip 16 and the sheath tip 26.

To insure complete ablation of the target endometrial tissue in the uterus of a female patient, it is helpful to employ a unique technique for placement of the cryosurgical probe and subsequent sequencing of the functions of the probe. In this method, a stepwise approach is used to position the cryosurgical probe in either one or two symmetric physical orientations within the endometrial cavity of the uterus, depending upon the volume of the uterus and the location of the tissue to be frozen.

Initially, following ultrasound assessment of the uterine cavity for specific physical features such as size, volume and presence of neoplasms, an appropriate one of two positioning techniques is chosen. The appropriate specific positioning technique is determined by uterine cavity size. For a uterine cavity size <40 mm in lateral width, a single position "midline freeze" technique is chosen. For a uterine cavity size $\geq$40 mm in lateral width, a two position "angled freeze" technique is chosen.

Figure 15:
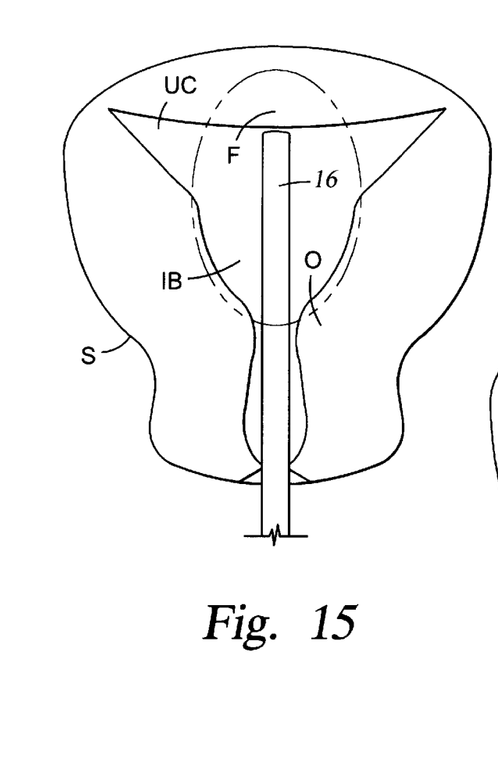
FIG. 15 is a schematic view of the cryosurgical probe positioning used in the midline freeze technique, according to the present invention.

For the single position, midline freeze technique, the cryosurgical probe 10 is advanced through the cervical os O under imaging guidance, until the distal cold tip 16 of the probe 10 is positioned along the saggital plane of the uterus at the fundus F as shown in FIG. 15. Ultrasound guidance at a frequency of 3 to 5 MHz is shown to be effective for visualization of the uterine cavity UC and probe tip 16, because of their respective echogenicity. Once the desired position of the probe tip 16 is visually verified, the freeze mode of the cryosurgical probe 10 is activated, to generate extreme cold temperatures at the distal cold tip 16. This freeze cycle is maintained for 3 to 7 minutes, or, until an ice ball IB is created with an adequate radial dimension from the longitudinal axis of the cryosurgical probe 10, to freeze the adjacent uterine cavity tissue. Ultrasound visualization also can be used to monitor ice ball growth. Activation of the freeze mode of the probe 10 is maintained for the aforementioned duration, until the outer edge of the ice ball, or ice front, reaches the serosal surface S of the uterine cavity UC, or, until initial ice ball dimensions approach 20 to 40 mm in diameter and 40 to 70 mm in length. Data has shown that the zone of endometrial tissue destruction is 3 to 5 mm radially behind the ice front; therefore, visualization of the ice ball IB allows the physician to avoid destruction of tissue in undesired areas. Freezing of human uterine cavity tissue results in adherence of the cryosurgical probe tip 16 to the endometrial tissue. Therefore, subsequent to the freeze, the heat mode of the cryosurgical probe 10 is activated by energizing the probe heater at the probe tip, to promote thawing of a thin layer of the tissue immediately adjacent to the cold tip 16, and to allow probe removal.

Figure 16:
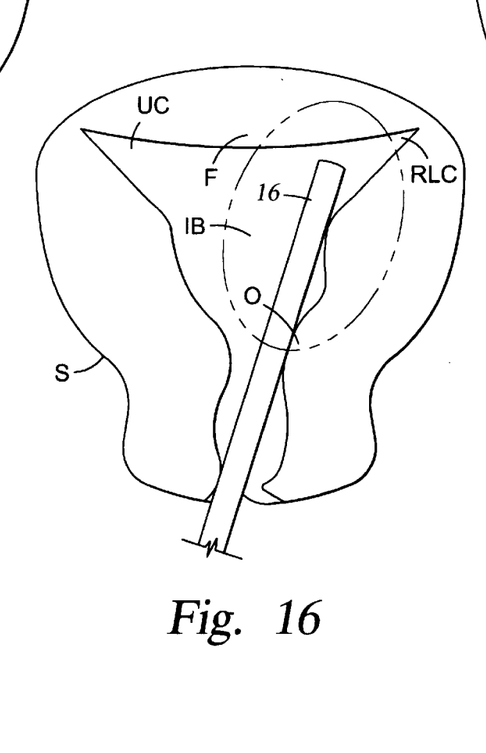
FIG. 16 is a schematic view of one position of the cryosurgical probe, as used in the angled freeze technique, according to the present invention.

For the two position, angled freeze technique, the cryosurgical probe 10 is advanced through the cervical os O under imaging guidance, as described above, until the distal cold tip 16 is positioned along a plane of angular offset at the fundus F in the left or right lateral cornu RLC as shown in FIG. 16. Although FIG. 16 shows the probe tip 16 angled toward the right lateral cornu RLC, the specific left or right lateral orientation used first is not significant. As in the midline technique, ultrasound visualization is used to verify the desired positioning of the probe cold tip 16. Once the desired position of the probe cold tip 16 is verified, the freeze mode of the probe 10 is activated for 3 to 7 minutes, or, until an ice ball IB is created with an adequate radial dimension from the longitudinal axis of the cryosurgical probe 10, to freeze the adjacent uterine cavity tissue. Ultrasound visualization can be used here, as in the midline technique, to monitor ice ball growth. Activation of the freeze mode of the probe 10 is maintained for the aforementioned duration, until the outer edge of the ice ball IB, or ice front, reaches the serosal surface S of the uterine cavity UC, or, until initial ice ball dimensions approach 20 to 40 mm in diameter and 40 to 70 mm in length. After completion of the first angled freeze, an injection of 3 to 5 ml of 0.9%, sterile, NaCl solution (normal saline) may be delivered through the irrigation port near the probe tip 16. This saline irrigation has been shown to promote additional tissue thaw at the proximal portion of the ice ball adjacent the cervical os O. Additional thawing of the proximal portion of the ice ball IB is desirable in the angled freeze method, to facilitate the repositioning of the probe 10 within the uterine cavity UC.

Figure 17:
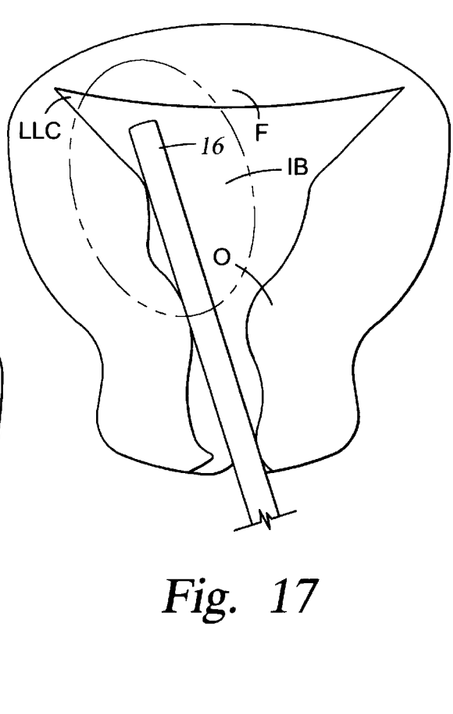
FIG. 17 is a schematic view of another position of the cryosurgical probe, as used in the angled freeze technique, according to the present invention.

Subsequently, the cryosurgical probe cold tip 16 is again advanced through the cervical os O until placement at the opposing lateral cornu at the fundus is achieved, such as the left lateral cornu LLC, as shown in FIG. 17. It can be seen that, in this second position, the probe 10 passes through the thawed proximal portion of the original ice ball. Ultrasound guidance is again used for position visualization. Once the second position is verified, the freeze mode of the probe 10 is again activated for the aforementioned duration, until the aforementioned ice ball dimension features are again achieved. It can be seen that this results in the freezing of a V-shaped, angled, ice ball in the uterine tissue. Subsequently, the heat mode of the probe 10 is again activated for said tissue thaw, probe removal and completion of the procedure.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. A method for cryogenic ablation of endometrial tissue in the uterus of a patient, said method comprising:

providing a probe having a cannula with a heat transfer element and an irrigation fluid flow path;

inserting said probe cannula into a uterus of a patient to position said heat transfer element adjacent to a selected area of endometrial tissue within the uterus;

providing a cryogenic refrigerant via said cannula to cool said heat transfer element to a sufficiently low temperature to cryogenically ablate said selected area of endometrial tissue;

heating said heat transfer element to a temperature sufficient to release said heat transfer element from frozen endometrial tissue; and providing irrigation fluid via said fluid flow path to said area of endometrial tissue, subsequent to heating of said heat transfer element, to assist in release of said heat transfer element from frozen tissue.

2. A method as recited in claim 1, wherein said heating of said heat transfer element is accomplished by energizing an electrical heating element adjacent to said heat transfer element.

3. A method for cryogenic ablation of endometrial tissue in the uterus of a patient, said method comprising:

providing a probe having a cannula with a heat transfer element, and an irrigation fluid flow path;

inserting said probe cannula into a uterus of a patient to position said heat transfer element adjacent to a first lateral cornu of the uterus;

providing a cryogenic refrigerant via said cannula to cool said heat transfer element to a sufficiently low temperature to cryogenically ablate a first selected area of endometrial tissue along a first lateral side of the uterus;

heating said heat transfer element to a temperature sufficient to release said heat transfer element from frozen endometrial tissue;

providing irrigation fluid via said fluid flow path to a proximal portion of said area of frozen endometrial tissue, subsequent to heating of said heat transfer element, to thaw said proximal portion of said area of frozen endometrial tissue;

repositioning said probe cannula in the uterus to position said heat transfer element adjacent to a second lateral cornu of the uterus;

providing a cryogenic refrigerant via said cannula to cool said heat transfer element to a sufficiently low temperature to cryogenically ablate a second selected area of endometrial tissue along a second lateral side of the uterus; and heating said heat transfer element to a temperature sufficient to release said heat transfer element from frozen endometrial tissue.

4. A method as recited in claim 3, wherein said heating of said heat transfer element is accomplished by energizing an electrical heating element adjacent to said heat transfer element.

* * * * *